United States Patent
Walter et al.

(10) Patent No.: US 11,173,299 B2
(45) Date of Patent: Nov. 16, 2021

(54) ELECTRODE LEADS CONFIGURED TO ENGAGE WITH A FIXING ELEMENT AND METHODS FOR MANUFACTURING THE SAME

(71) Applicant: Advanced Bionics AG, Staefa (CH)

(72) Inventors: Jeryle L. Walter, Valencia, CA (US); Enrique Gandaria, Santa Clarita, CA (US); Sung Jin Lee, Valencia, CA (US); James G. E. Smith, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 85 days.

(21) Appl. No.: 16/208,355

(22) Filed: Dec. 3, 2018

(65) Prior Publication Data

US 2020/0171300 A1 Jun. 4, 2020

(51) Int. Cl.
*A61N 1/05* (2006.01)
*A61N 1/36* (2006.01)
*A61N 1/375* (2006.01)

(52) U.S. Cl.
CPC ....... *A61N 1/0541* (2013.01); *A61N 1/36038* (2017.08); *A61N 1/37518* (2017.08)

(58) Field of Classification Search
CPC .... A61N 1/05; A61N 1/0541; A61N 1/36038; A61N 1/37518
USPC ........................................................ 607/137
See application file for complete search history.

(56) References Cited

U.S. PATENT DOCUMENTS

| | | | |
|---|---|---|---|
| 5,674,272 A | 10/1997 | Bush et al. | |
| 5,683,447 A | 11/1997 | Bush et al. | |
| 8,315,704 B2 | 11/2012 | Jaax et al. | |
| 2008/0208306 A1* | 8/2008 | Rutten | A61N 1/05 607/127 |
| 2012/0029335 A1 | 2/2012 | Sudam et al. | |
| 2013/0204075 A1* | 8/2013 | Allen | A61B 17/3468 600/30 |
| 2014/0005675 A1* | 1/2014 | Swoyer | A61N 1/0551 606/129 |
| 2016/0096012 A1* | 4/2016 | Dhanasingh | A61N 1/0541 607/137 |
| 2016/0199638 A1* | 7/2016 | Xu | A61N 1/36036 607/137 |
| 2018/0236250 A1 | 8/2018 | Clabeaux | |

* cited by examiner

*Primary Examiner* — Michael W Kahelin
(74) *Attorney, Agent, or Firm* — ALG Intellectual Property, LLC

(57) ABSTRACT

An exemplary electrode lead includes a flexible body formed of a flexible insulating material, an electrode contact disposed on an outer surface of the flexible body, and a strand that includes a first end portion, a second end portion, and a loop that is provided between the first end portion and the second end portion and that protrudes from the flexible body. The loop is configured to engage with a fixing element that is configured to attach the loop to tissue within a recipient to secure the electrode lead within the recipient. Corresponding methods for manufacturing an electrode lead are also described.

20 Claims, 12 Drawing Sheets

ELECTRODE LEADS CONFIGURED TO ENGAGE WITH A FIXING ELEMENT AND METHODS FOR MANUFACTURING THE SAME

BACKGROUND INFORMATION

Cochlear implant systems are used to provide, restore, and/or improve the sense of hearing to recipients with severe or profound hearing loss. A key component of a cochlear implant system is an electrode lead that is inserted into a cochlea of the recipient in a delicate surgical procedure referred to herein as an "insertion procedure." Because insertion procedures are difficult and may result in sub-optimal function of the cochlear implant system, cochlear trauma, or other harm if not done with extreme care, surgeons and other people involved in insertion procedures may carefully monitor and track the electrode lead by identifying its position and insertion path with respect to the cochlea during and after the insertion procedure to ensure that the electrode lead is positioned correctly.

Unfortunately, after the electrode lead is positioned within the cochlea, certain events may occur that cause the electrode lead to shift from an inserted position achieved during the insertion procedure to another position within the cochlea. For example, a traumatic injury to the head of the recipient or even something as common as the recipient sneezing may cause the electrode lead to shift from the inserted position to another position. These and similar events may result in loss of function or sub-optimal function of the cochlear implant system because the electrode lead may not be able to adequately provide electrical stimulation to the recipient at the shifted position. In some cases, such a shift of position of the electrode lead may undesirably require a surgery to reposition the electrode lead.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Electrode leads configured to engage with a fixing element and methods for manufacturing the same are described herein. As will be described in more detail below, an exemplary electrode lead described herein includes a flexible body formed of a flexible insulating material, an electrode contact disposed on an outer surface of the flexible body, and a strand that includes a first end portion provided within the flexible body, a second end portion provided within the flexible body, and a loop that is provided between the first end portion and the second end portion and that protrudes from the flexible body. The loop is configured to engage with a fixing element that is configured to attach the loop to tissue within a recipient to secure the electrode lead within the recipient.

In certain examples, electrode leads such as those described herein may include a plurality of loops. For example, the plurality of loops may include a first loop, a second loop, and a third loop. Each of the loops may be radially separated from each other along a length of the flexible body and/or about the circumference of the flexible body. With such a configuration, surgeons and others involved with insertion procedures may easily select whichever one or more of the plurality of loops is positioned most conveniently to engage with the fixing element without having to rotate and/or reposition the electrode lead.

The electrode leads described herein may provide various benefits to cochlear implant recipients, as well as to surgeons and others involved with insertion procedures. For example, because the electrode leads described herein include one or more loops configured to engage with a fixing element, the electrode leads are less susceptible to shifting position after the insertion procedure. In addition, electrode leads such as those described herein may facilitate convenient identification and selection of a loop to engage with a fixing element during an insertion procedure because the loop is easily viewable by a surgeon. Moreover, electrode leads such as those described herein may have increased mechanical strength in at least a region that includes the loop, which results in a decreased likelihood that the electrode lead and/or loop will be damaged due to, for example, an impact to the recipient's head. Accordingly, cochlear implant systems that use electrode leads such as those described herein are more robust and potentially have a longer operational life than cochlear implant systems that use conventional electrode leads.

Various embodiments will now be described in more detail with reference to the figures. The disclosed leads and methods may provide one or more of the benefits mentioned above and/or various additional and/or alternative benefits that will be made apparent herein.

Figure 1:
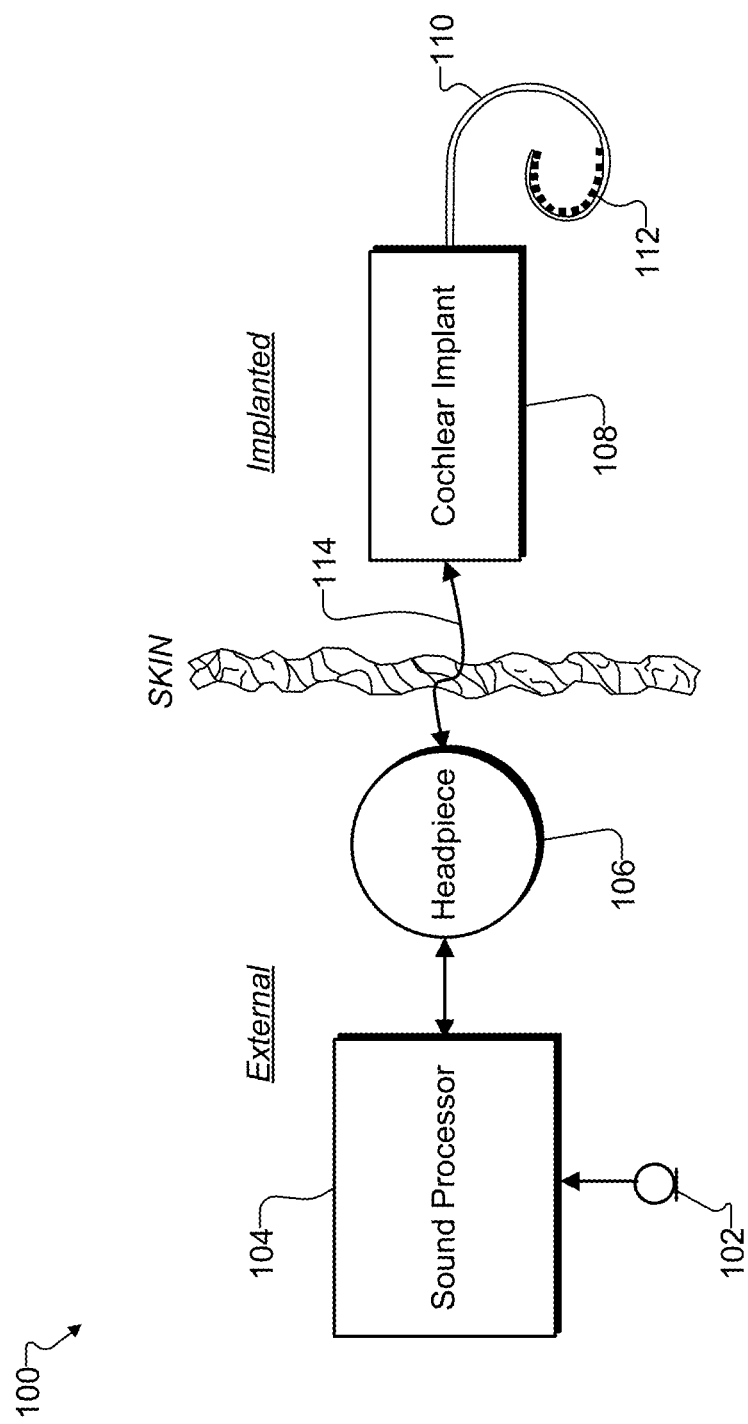
FIG. 1 illustrates an exemplary cochlear implant system according to principles described herein.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110. Electrode lead 110 may include an array of electrodes 112 disposed on a distal portion of electrode lead 110 and that are configured to be inserted into the cochlea to stimulate the cochlea after the distal portion of electrode lead 110 is inserted into the cochlea. It will be understood that one or more other electrodes (e.g., including a ground electrode, not explicitly shown in FIG. 1) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. Various embodiments of electrode lead 110 will be described herein. Additional or alternative components may be included within cochlear implant system 100 as may serve a particular implementation. For example, a pre-curved electrode lead and/or a straight electrode lead may alternatively be used in connection with cochlear implant 108.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a device like the Clinical Programming Interface ("CPI") device from Advanced Bionics, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the recipient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
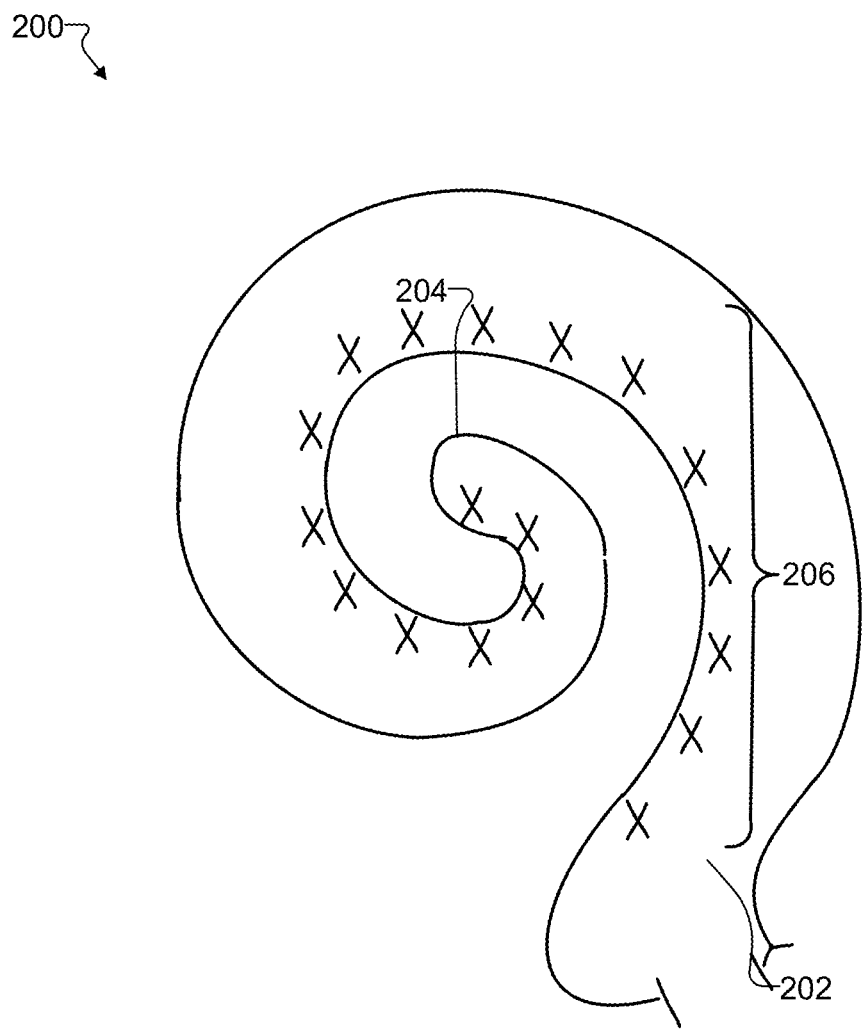
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the recipient perceiving relatively low frequencies and electrical stimulation applied by way of electrodes disposed within the basal region (i.e., "basal electrodes") may result in the recipient perceiving relatively high frequencies. The delineation between the apical and basal electrodes on a particular electrode lead may vary depending on the insertion depth of the electrode lead, the anatomy of the recipient's cochlea, and/or any other factor as may serve a particular implementation.

After electrode lead 110 is inserted into cochlea 200, electrodes 112 may be used by cochlear implant system 100 to provide electrical stimulation to one or more stimulation sites within the recipient. However, if electrode lead 110 changes position (e.g., is pulled by some amount in a direction out of cochlea 200) after the insertion procedure, one or more of electrodes 112 may no longer be in a position to provide adequate electrical stimulation to the one or more stimulation sites.

As will be described herein, to prevent electrode lead 110 from shifting within the recipient after the insertion procedure, electrode lead 110 may include a strand having a loop that protrudes from electrode lead 110 and that is configured to engage with a fixing element that is configured to attach the loop to tissue within the recipient. As used herein, "tissue" refers to any soft tissue, bone, or any combination thereof included within the recipient. Electrode lead 110 may be configured to engage with any suitable fixing element as may serve a particular implementation. As used herein, "a fixing element" refers to any device configured to engage with a loop of a strand to secure electrode lead 110 in place within the recipient. For example, a fixing element may include a suture, a staple, a bone screw, and/or any other suitable device. In certain examples, a fixing element may be configured to engage with the loop and the tissue within the recipient at substantially the same time to secure electrode lead 110 in place. Alternatively, a fixing element may be configured to be secured to the tissue within the recipient first and then the loop may engage with the fixing element afterwards in any suitable manner to secure electrode lead 110 in place.

A strand that includes one or more loops such as those described herein may be configured in any manner as may suit a particular implementation. For example, a strand may include either a single loop or a plurality of loops. Alternatively, a plurality of separate strands may be provided where each separate strand included in the plurality of separate strands includes one or more loops. Loops such as those described herein may be provided at any suitable position between a distalmost tip of electrode lead 110 and a position where electrode lead 110 enters cochlear implant 108. Additionally or alternatively, one or more loops may be provided at any suitable position between a most proximal electrode included in electrodes 112 and the position where electrode lead 110 enters cochlear implant 108.

A strand that forms one or more loops such as those described herein may be made of any suitable material as may serve a particular implementation. For example, a strand may be formed of a biocompatible polymer such as polyethylene or polyethylene terephthalate. In certain alternative examples, a strand may be formed of a material that is relatively more stiff than polyethylene or polyethylene terephthalate. For example, the strand may be formed of Nitinol, polyetheretherketone (PEEK) tubing, or a drawn filled tube (DFT) biocompatible wire in certain implementations. In certain examples, a strand may be formed of a malleable material to allow a surgeon to shape a loop formed in the strand in any suitable manner prior to and/or during an insertion procedure so that the loop conforms with the particular anatomy of a recipient and/or facilitates engagement with a fixing element. For example, a loop formed of Nitinol may be bent by a surgeon to have any suitable shape and/or angle with respect to electrode lead 110 so that the loop better conforms with the particular anatomy of a recipient. Various exemplary loops that may be used to secure electrode lead 110 within the recipient will now be described with reference to FIGS. 3-11.

Figure 3:
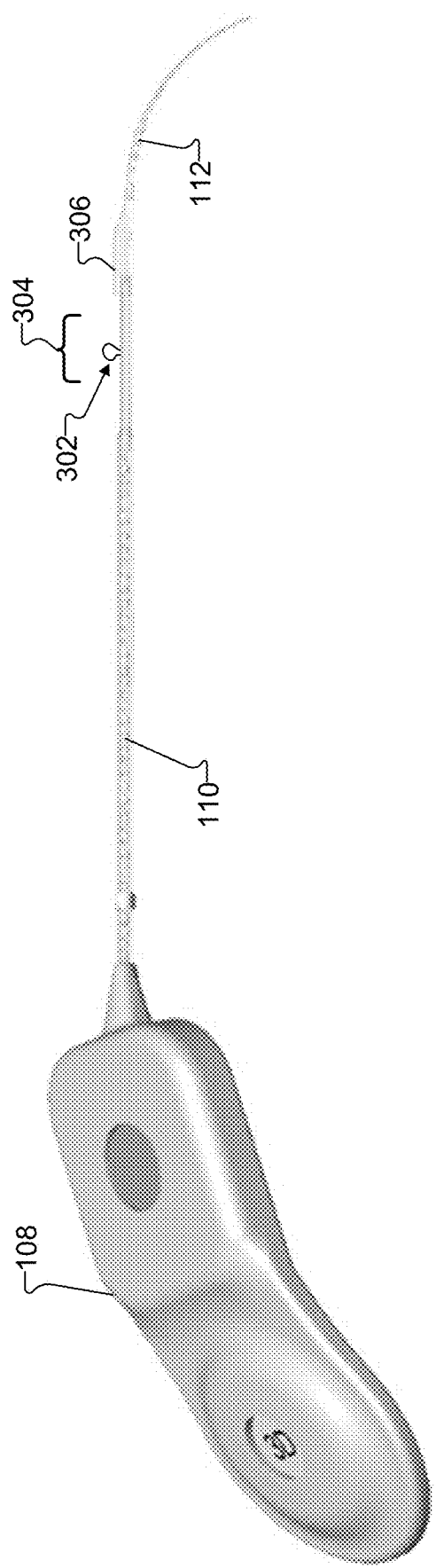
FIG. 3 illustrates exemplary components of the cochlear implant system that are configured to be implanted in a recipient according to principles described herein.

FIG. 3 illustrates an exemplary depiction of components of cochlear implant system 100 that are configured to be implanted in a recipient. For example, FIG. 3 shows cochlear implant 108 communicatively coupled to electrode lead 110 with electrodes 112 disposed along electrode lead 110. As shown in FIG. 3, electrode lead 110 includes a strand 302 that has a portion that protrudes radially from electrode lead 110 in a region 304 of electrode lead 110. Region 304 may be provided along any suitable portion of electrode lead 110. In some instances, region 304 may generally be considered as a region of electrode lead 110 that is provided between electrodes 112 and cochlear implant 108. In certain examples, region 304 may be provided along a portion of electrode lead 110 that is positioned within the mastoid cavity of the recipient when electrode lead 110 is inserted within the recipient. In such examples, the surgeon may secure strand 302 in any suitable manner to tissue within the mastoid cavity to prevent electrode lead 110 from changing position after insertion.

In the example shown in FIG. 3, electrode lead 110 also includes a wing section 306 that has an enlarged diameter with respect to a remainder of electrode lead 110. Wing section 306 may serve a variety of functions, including, but not limited to, providing a structure which can be gripped by an insertion tool and securing electrode lead 110 within the cochlea in certain implementations.

Figure 4:
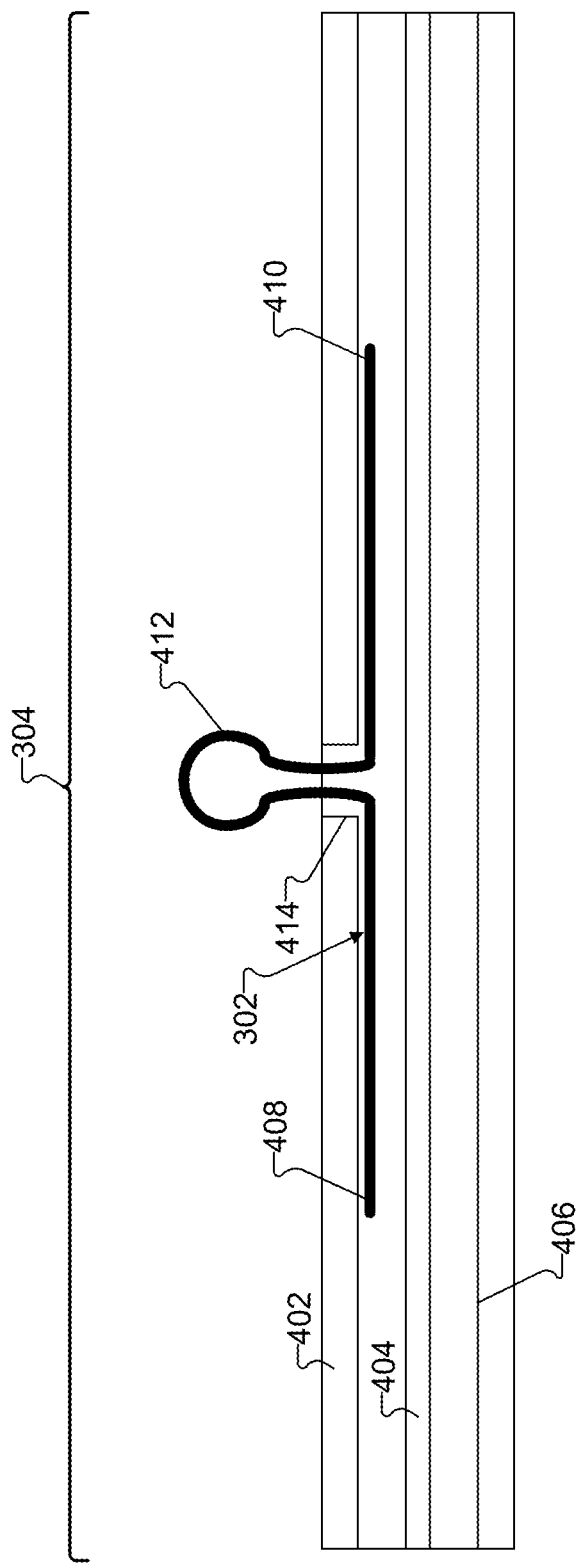
FIGS. 4-7 illustrate enlarged side views of regions of exemplary electrode leads having one or more loops according to principles described herein.

Strand 302 may be attached to electrode lead 110 in any suitable manner. FIG. 4 shows an enlarged side view of region 304 of electrode lead 110 according to one example that includes strand 302, a flexible body 402, and an electrode wire 404 that connects to an electrode contact (e.g., one of electrodes 112) disposed on an outer surface of flexible body 402. In the example shown in FIG. 4, flexible body 402 includes a flexible tube having a lumen 406 that is filled in with soft flexible material such as silicone. The soft flexible material filled within lumen 406 forms part of flexible body 402 and secures strand 302 and electrode wire 404 within flexible body 402. The features (e.g., electrode wire 404, lumen 406, etc.) provided inside electrode lead 110 are shown as being visible in FIG. 4 for illustrative purposes. It is understood that the material that forms flexible body 402 and/or that is provided within lumen 406 may be transparent or may be opaque in certain examples.

As shown in FIG. 4, strand 302 includes a first end portion 408 and a second end portion 410 that are provided within flexible body 402. In the example shown in FIG. 4, first end portion 408 of strand 302 extends along a length of flexible body 402 in a first direction (e.g., towards cochlear implant 108) and second end portion 410 of strand 302 extends along the length of flexible body 402 in a second direction (e.g., towards electrodes 112) that is opposite to the first direction. As shown in FIG. 4, a section of strand 302 forms a loop 412 that is provided between first end portion 408 and second end portion 410 and that protrudes from flexible body 402. Loop 412 may have any suitable size sufficient to allow a surgeon to attach a fixing element (not shown) through loop 412 and to tissue within the recipient.

Loop 412 may protrude from flexible body 402 in any suitable manner. In the example shown in FIG. 4, loop 412 extends through a hole 414 formed in flexible body 402 that may be filled in with a flexible biocompatible material such as silicone after loop 412 is provided through hole 414. In other examples, flexible body 402 may be formed in a mold such that strand 302 is embedded within flexible body 402 and loop 412 protrudes from a molded outer surface of flexible body 402.

Figure 5:
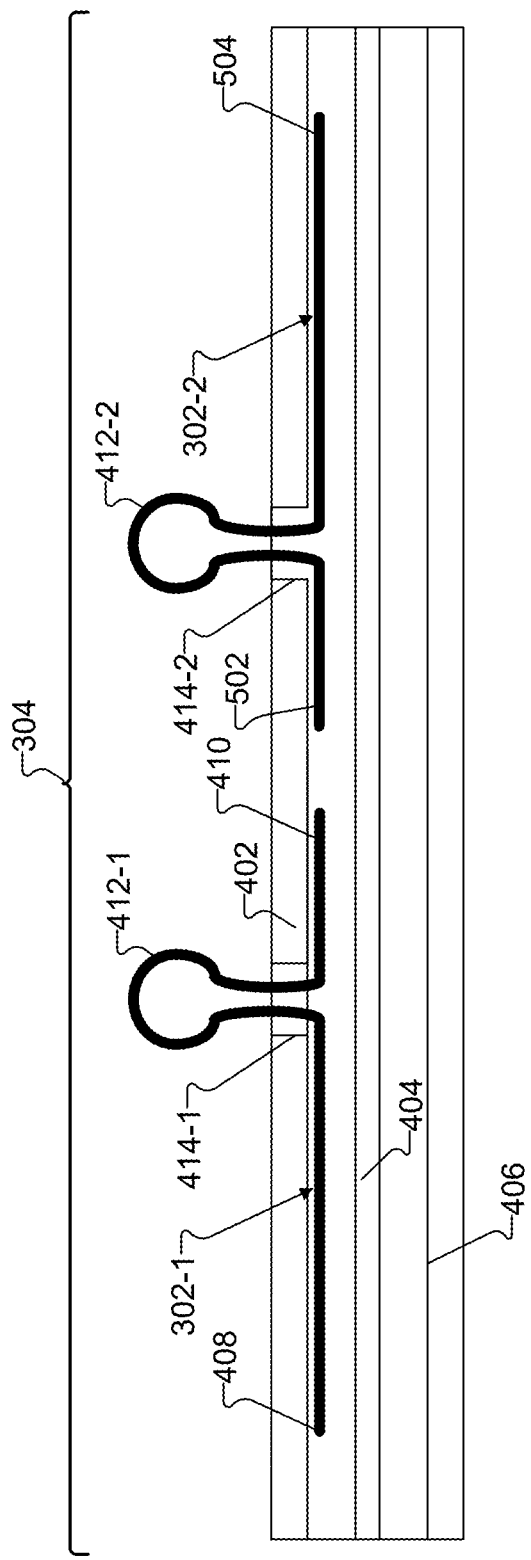

FIG. 5 shows a side view of an alternative implementation in which a plurality of strands 302 (e.g., strands 302-1 and 302-2) are provided within flexible body 402. As shown, strands 302-1 and 302-2 each include a loop 412 (e.g., loop 412-1 and loop 412-2) that protrudes radially from flexible body 402. In the example shown in FIG. 5, strand 302-1 is configured in a manner similar to strand 302 shown in FIG.

4. Similar to strand 302-1, strand 302-2 includes a first end portion 502 and a second end portion 504 that are provided within flexible body 402. First end portion 502 of strand 302-2 extends along a length of flexible body 402 in a first direction (e.g., towards cochlear implant 108) and second end portion 504 of strand 302-2 extends along the length of flexible body 402 in a second direction (e.g., towards electrodes 112) that is opposite to the first direction. A section of strand 302-2 forms loop 412-2 that is provided between first end portion 502 and second end portion 504 and that protrudes from flexible body 402 through a hole 414-2.

As shown in FIG. 5, strand 302-2 is positioned within flexible body 402 such that loop 412-2 protrudes from flexible body 402 at a first location (e.g., at hole 414-2) along the length of flexible body 402 and loop 412-1 protrudes from flexible body 402 at a second location (e.g., at hole 414-1) along the length of flexible body 402. In this regard, loop 412-1 and loop 412-2 may be considered as being staggered along a length of flexible body 402.

In the example shown in FIG. 5, strand 302-1 is spaced apart in a longitudinal direction (i.e., a horizontal direction in FIG. 5) of flexible body 402 from strand 302-2 such that strand 302-1 does not overlap strand 302-2 along a longitudinal direction. With such a configuration, it may be possible to avoid unduly increasing the diameter of flexible body due to the inclusion of a plurality of strands.

Figure 6:
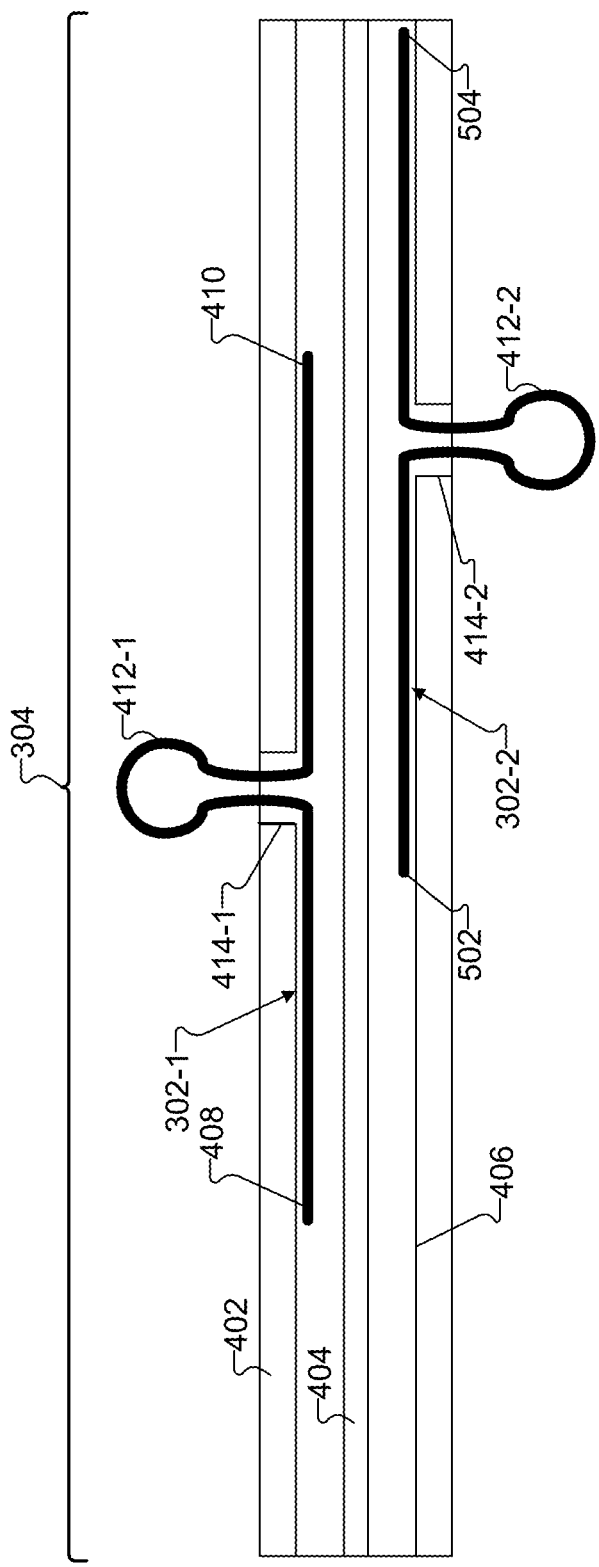

FIG. 6 shows a side view of an alternative implementation in which a plurality of separate strands 302 (e.g., strands 302-1 and 302-2) are provided that have loops 412 (e.g., loops 412-1 and 412-2) that are radially separated from each other about a circumference of flexible body 402. As shown in FIG. 6, loop 412-2 protrudes from hole 414-2, which is provided on an opposite side of flexible body 402 than hole 414-1 such that loop 412-2 protrudes from flexible body 402 in a different direction than loop 412-1. In the example shown in FIG. 6, a portion of strand 302-1 overlaps a portion of strand 302-2 along the longitudinal direction of flexible body 402. Strands 302 may be considered as partially overlapping one another in FIG. 6 because, when strands 302 are followed from left to right in FIG. 6, strand 302-2 begins before strand 302-1 ends. However, it is understood that in certain examples each separate strand may be spaced apart in the longitudinal direction of the flexible body from an adjacent strand, such as is shown in FIG. 5 where there is a gap in the longitudinal direction between second end portion 410 of strand 302-1 and first end portion 502 of strand 302-2.

Although FIGS. 5 and 6 only show two separate strands, it is understood that any number of strands may be provided within flexible body 402 as may serve a particular implementation. For example, a third strand may also be provided within flexible body in any suitable manner such as described herein.

Figure 7:
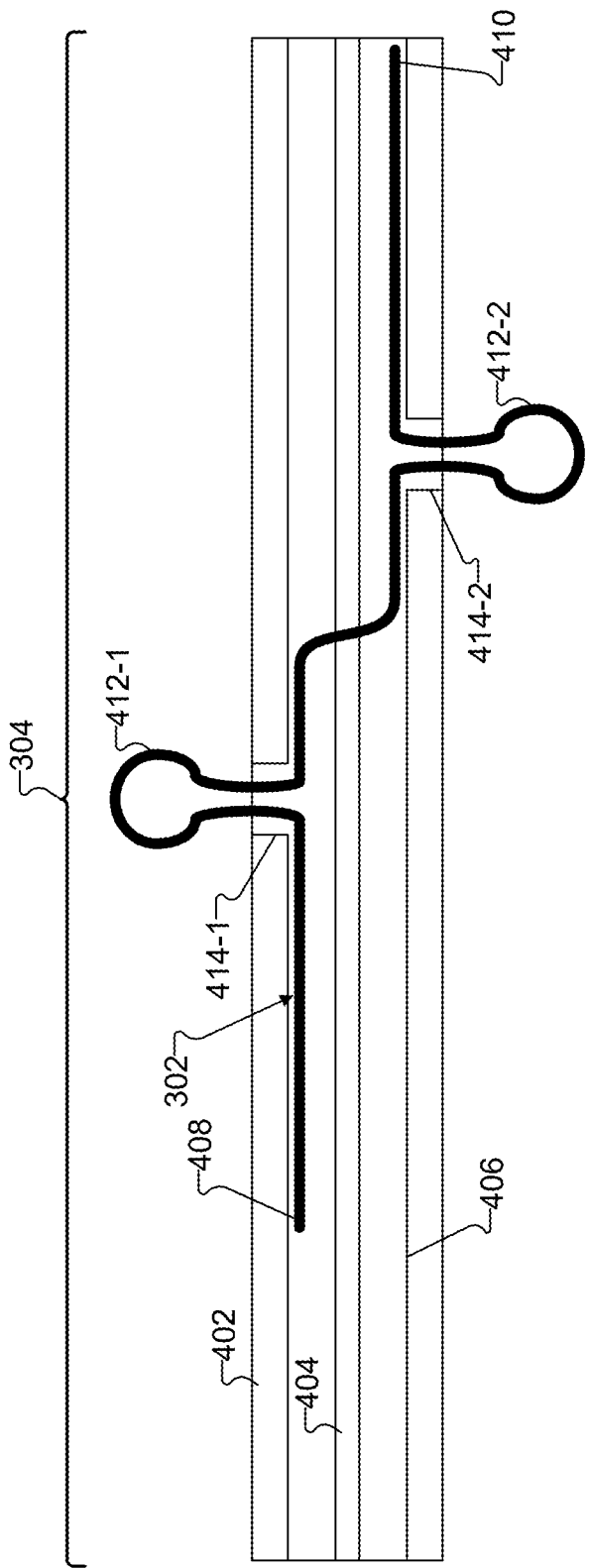

FIG. 7 illustrates a side view of an alternative implementation in which two loops are formed from a single strand. As shown in FIG. 7, a second loop 412-2 is provided between loop 412-1 and second end portion 410 of strand 302. In the example shown in FIG. 7, strand 302 turns within lumen 406 such that loop 412-2 protrudes from a different side of flexible body 402 than loop 412-1. In certain alternative examples, loop 412-2 may protrude from the same side of flexible body 402 as loop 412-1. Although the example shown in FIG. 7 only shows strand 302 as including two loops, it is understood that a single strand may include three or more loops in certain implementations.

Similar to FIG. 4, the features (e.g., electrode wire 404, lumen 406, etc.) provided inside electrode lead 110 are shown as being visible in FIG. 5-7 for illustrative purposes.

Figure 8:
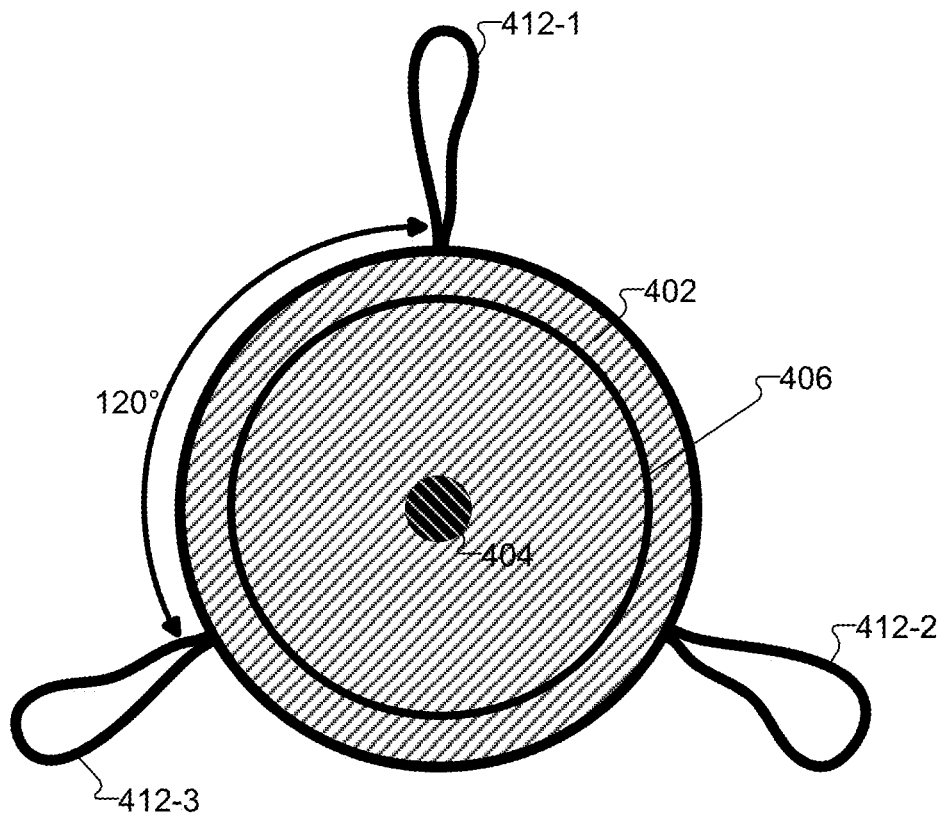
FIGS. 8 and 9 are an exemplary cross sections of electrode leads according to principles described herein.
Figure 9:
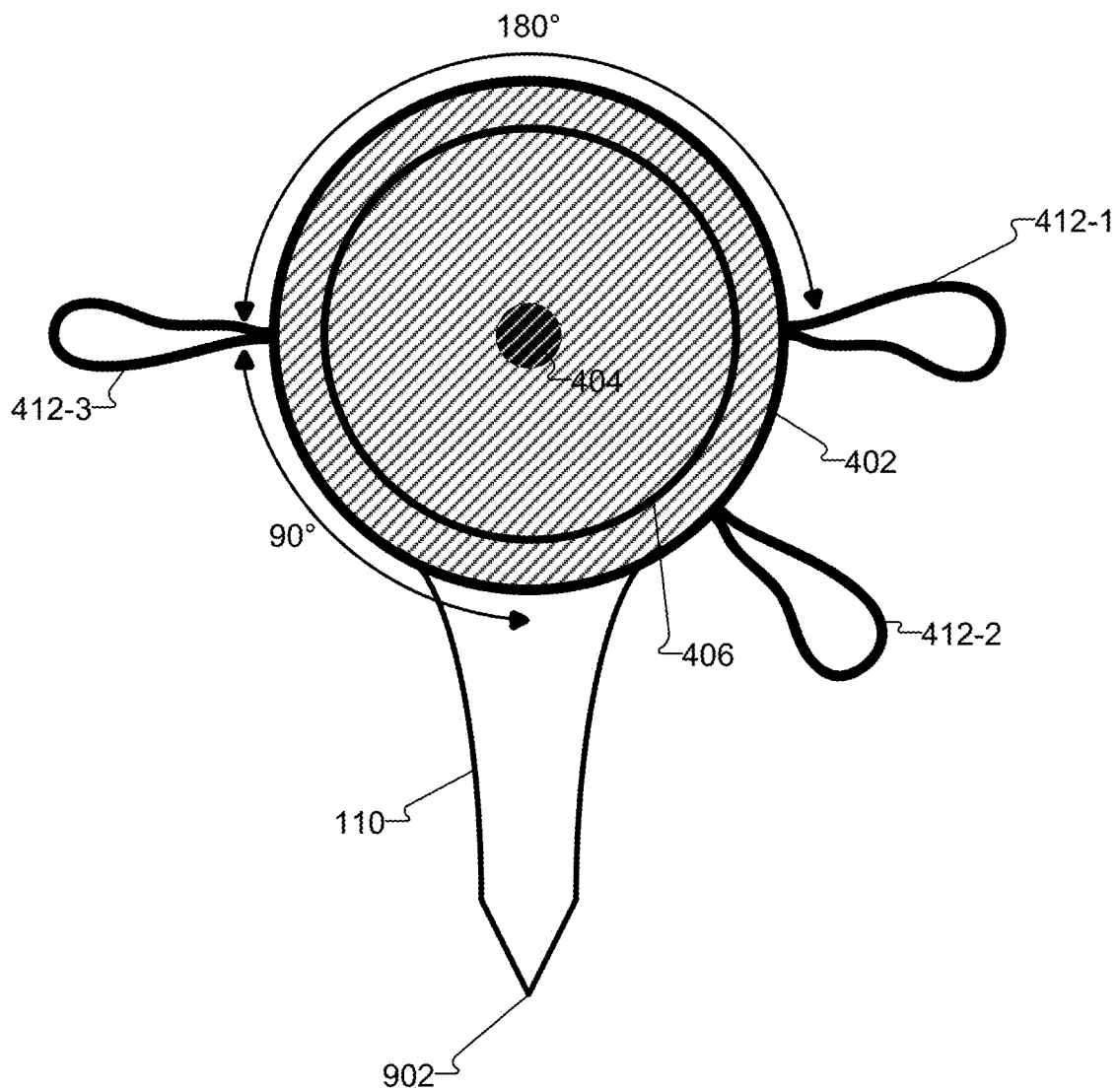

FIG. 8 shows a cross-section of electrode lead 110 according to one example that is taken in a plane that is perpendicular to an extending direction of electrode lead 110. As shown in FIG. 8 electrode lead 110 includes three loops that are spaced apart from each other about a circumference of flexible body 402. In the example shown in FIG. 8, electrode lead 110 includes a first loop 412-1, a second loop 412-2, and a third loop 412-3 that are each provided about a circumference of flexible body 402. Loops 412-1, 412-2, and 412-3 protrude from flexible body 402 at positions that are spaced apart equally (i.e., by 120 degrees) about the circumference of flexible body 402 to facilitate the surgeon using one or more of loops 412 to secure the electrode lead within the recipient. In certain alternative implementations, electrode lead 110 may include a plurality of strands that have loops that are radially separated from each other by different (i.e., not equal) angles about the circumference of flexible body 402. To illustrate, FIG. 9 shows a cross-section of electrode lead 110 according to another example that is taken in a plane that is perpendicular to an extending direction of electrode lead 110. In the example shown in FIG. 9, electrode lead 110 includes a first loop 412-1, a second loop 412-2, and a third loop 412-3 that are each provided about a circumference of flexible body 402. As shown in FIG. 9, loops 412-1 and 412-3 protrude from flexible body 402 at positions that are spaced apart from each other by 180 degrees about the circumference of flexible body 402. However, loop 412-2 protrudes from a position that is approximately 45 degrees from loop 412-1 and approximately 135 degrees from loop 412-3. The position at which loop 412-2 protrudes from flexible body 402 in FIG. 9 is provided for illustrative purposes only. It is understood that loop 412-2 may be provided at any suitable position with respect to loops 412-1 and 412-3 and electrode lead 110 as may serve a particular implementation.

In certain examples, loops 412-1, 412-2, and 412-3 may be arranged so as to have a predefined angular relationship with respect to a curved portion of electrode lead 110. To illustrate, in the example shown in FIG. 9, electrode lead 110 extends into the plane of the paper and curves downward towards a distal tip 902 of electrode lead 110 beyond the plane of the paper. The portion labeled with the reference numeral "110" in FIG. 9 corresponds to an exterior surface of electrode lead 110 that is visible due to the curvature of electrode lead 110. As shown in FIG. 9, loops 412-1 and 412-3 are each provided at a right angle with respect to a center line of the downwardly curving portion of electrode lead 110. Loop 412-2 on the other hand is provided at approximately a 45 degree angle with respect to the center line of the downwardly curving portion of electrode lead 110.

In certain examples, the configuration of loops 412-1 and 412-3 shown in FIG. 9 may facilitate the surgeon positioning electrode lead 110 within the recipient. For example, loops 412-1 and 412-3 may be formed of a relatively stiff material such as Nitinol, a DFT biocompatible wire, or PEEK tubing that provides torsional resistance to reduce twisting of electrode lead 110 and control the way electrode lead 110 sits with respect to the cochlea of the recipient during insertion. Loop 412-2 may be formed of the same material or a different material than loops 412-1 and 412-3 and may facilitate the surgeon using a fixing element to secure electrode lead 110 in position after insertion within the recipient. Additionally or alternatively, the surgeon may attach a fixing element to one or more of loops 412-1 and 412-3 to secure electrode lead 110 within the recipient.

In certain implementations, the engagement of a loop with a fixing element may result in increased stress to the wall of the flexible tube of flexible body 402. Such increased stress may result in the wall of the flexible tube tearing out. Accordingly, in certain examples, a plurality of reinforcing elements may be provided in a region of electrode lead 110 that includes strand 302 to strengthen electrode lead 110 and prevent such tearing out of the wall of the flexible tube. Such reinforcing elements may be provided along any suitable length of flexible body 402 as may serve a particular implementation. For example, such reinforcing elements may be provided along an entire length of flexible body 402. Alternatively, such reinforcing elements may only be provided within a region of flexible body 402 that includes strand 302.

Reinforcing elements such as those described herein may be configured in any manner as may suit a particular implementation. For example, a reinforcing element may include a mesh, wire, fiber, strand, ribbon, group of wires, group of fibers, group of strands, group of ribbons, etc., or any suitable combination thereof. A reinforcing element may be made of any suitable material as may serve a particular implementation. For example, a reinforcing element may be formed of a biocompatible polymer mesh, wire, fiber, strand, or ribbon. Examples of biocompatible polymers that may be used to form a reinforcing element include polyethylene, ultra-high-modulus polyethylene (UHMPE), PEEK, polyamide (nylon), etc.

Figure 10:
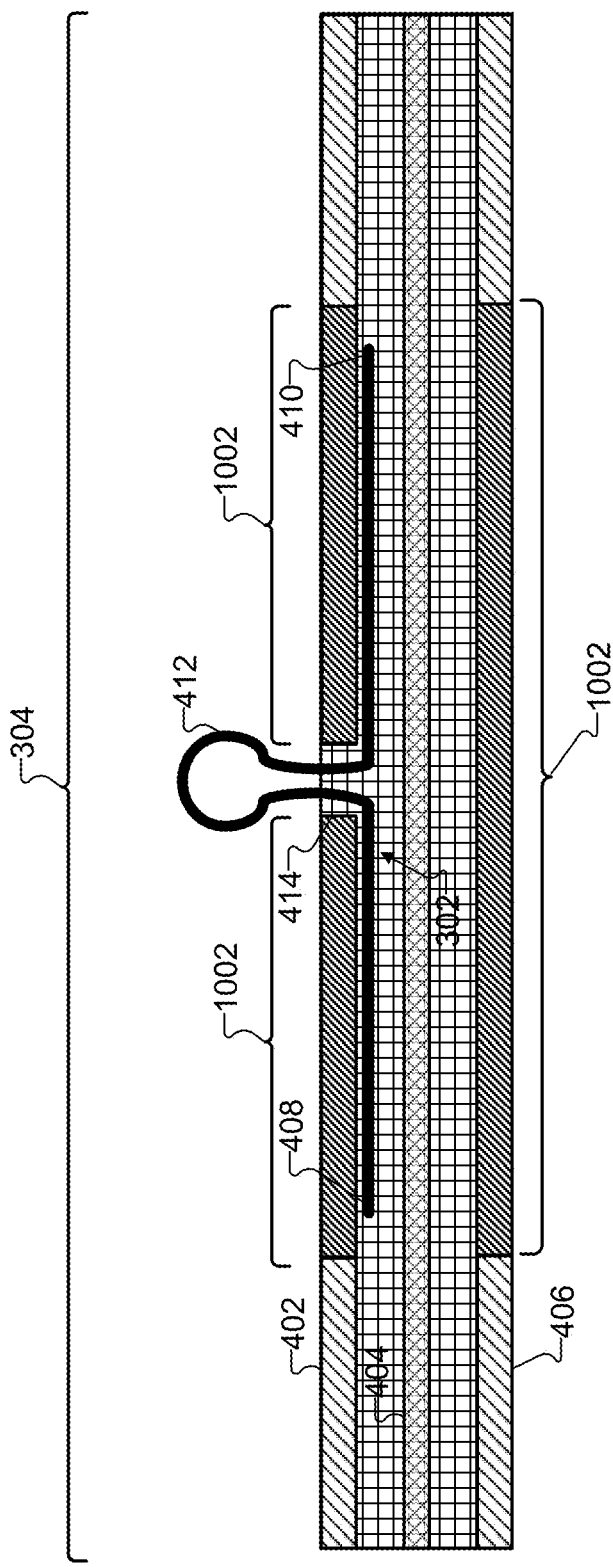
FIG. 10 illustrates a cross section of an enlarged region of an exemplary electrode lead having a loop according to principles described herein.

Such reinforcing elements may be provided within electrode lead 110 in any suitable manner. For example, one or more reinforcing elements may be embedded within flexible body 402 (e.g., within a wall of the flexible tube and/or within the soft flexible material filled within lumen 406). In certain examples, one or more reinforcing elements may be coiled within electrode lead 110. To illustrate, FIG. 10 shows an enlarged cross-sectional view of region 304 in which a plurality of reinforcing elements 1002 are provided. In the example shown in FIG. 10 reinforcing elements 1002 are coiled within a wall of the flexible tube of flexible body 402 on both sides of loop 412. Although FIG. 10 shows reinforcing elements 1002 as only being provided within region 304, it is understood that reinforcing elements 1002 may be provided along any suitable length of electrode lead 110 as may serve a particular implementation.

Figure 11:
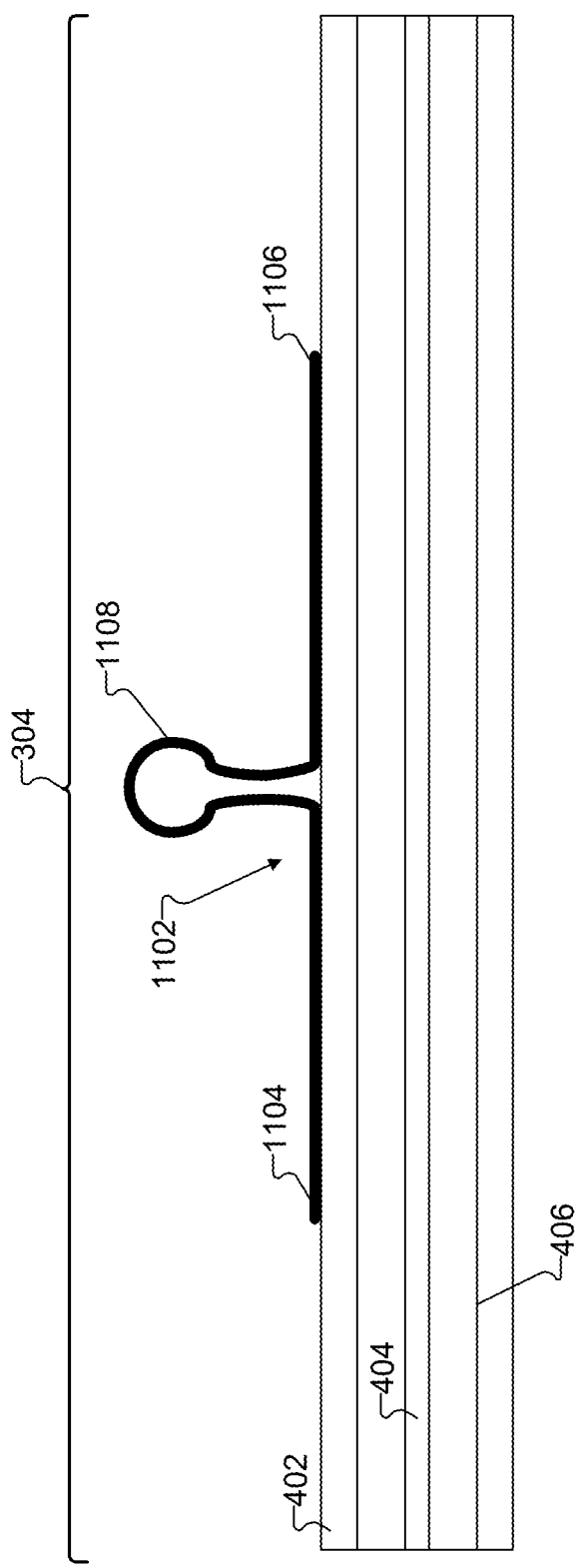
FIG. 11 illustrates another exemplary enlarged side view of a region of an exemplary electrode lead having a loop according to principles described herein.

In certain alternative examples, portions of a strand may be attached to an exterior surface of electrode lead 110. To illustrate, FIG. 11 shows an enlarged view of region 304 of electrode lead 110 that includes a strand 1102, flexible body 402, and electrode wire 404. In the example shown in FIG. 11, flexible body 402 includes a flexible tube having a lumen 406 that is filled in with soft flexible material such as silicone.

As shown in FIG. 11, strand 1102 includes a first end portion 1104 and a second end portion 1106 that are provided on the exterior surface of flexible body 402. In the example shown in FIG. 11, first end portion 1104 of strand 1102 extends along a length of flexible body 402 in a first direction (e.g., towards cochlear implant 108) and second end portion 410 of strand 302 extends along the length of flexible body 402 in a second direction (e.g., towards electrodes 112) that is opposite to the first direction. First end portion 1104 and second end portion 1106 may be secured to the exterior surface of flexible body 402 in any suitable manner. For example, a biocompatible silicone adhesive may be provided along the length of first end portion 1104 and second end portion 1106 to attached first end portion 1104 and second end portion 1106 to flexible body 402. As shown in FIG. 11, a section of strand 1102 forms a loop 1108 that is provided between first end portion 1104 and second end portion 1106 and that protrudes from flexible body 402. Loop 1108 may have any suitable size sufficient to allow a surgeon to attach a fixing element through loop 1106 and to tissue within the recipient (e.g., within the mastoid cavity).

In the example shown in FIG. 11, loop 1108 protrudes at a right angle from the exterior surface of flexible body 402. However, loop 1108 may protrude from flexible body at any suitable angle as may serve a particular implementation.

Although FIG. 11 only shows one loop, it is understood that any suitable number of loops may be provided in a manner similar to loop 1108 as may serve a particular implementation. For example, three strands with loops may be attached to an exterior surface of flexible body 402 and may be arranged with respect to each other in any suitable manner such as described herein.

The features (e.g., electrode wire 404, lumen 406, etc.) provided inside electrode lead 110 are shown as being visible in FIG. 11 for illustrative purposes. It is understood that the material that forms flexible body 402 and/or that is provided within lumen 406 may be transparent or may be opaque in certain examples.

In certain alternative examples, region 304 may be provided at wing section 306 such that strand 302 is secured within wing section 306. In such examples, wing section 306 may be formed of a biocompatible material (e.g., silicone) in an overmold process during which certain portions of strand 302 are embedded within the biocompatible material to secure strand 302 within wing section 306.

Figure 12:
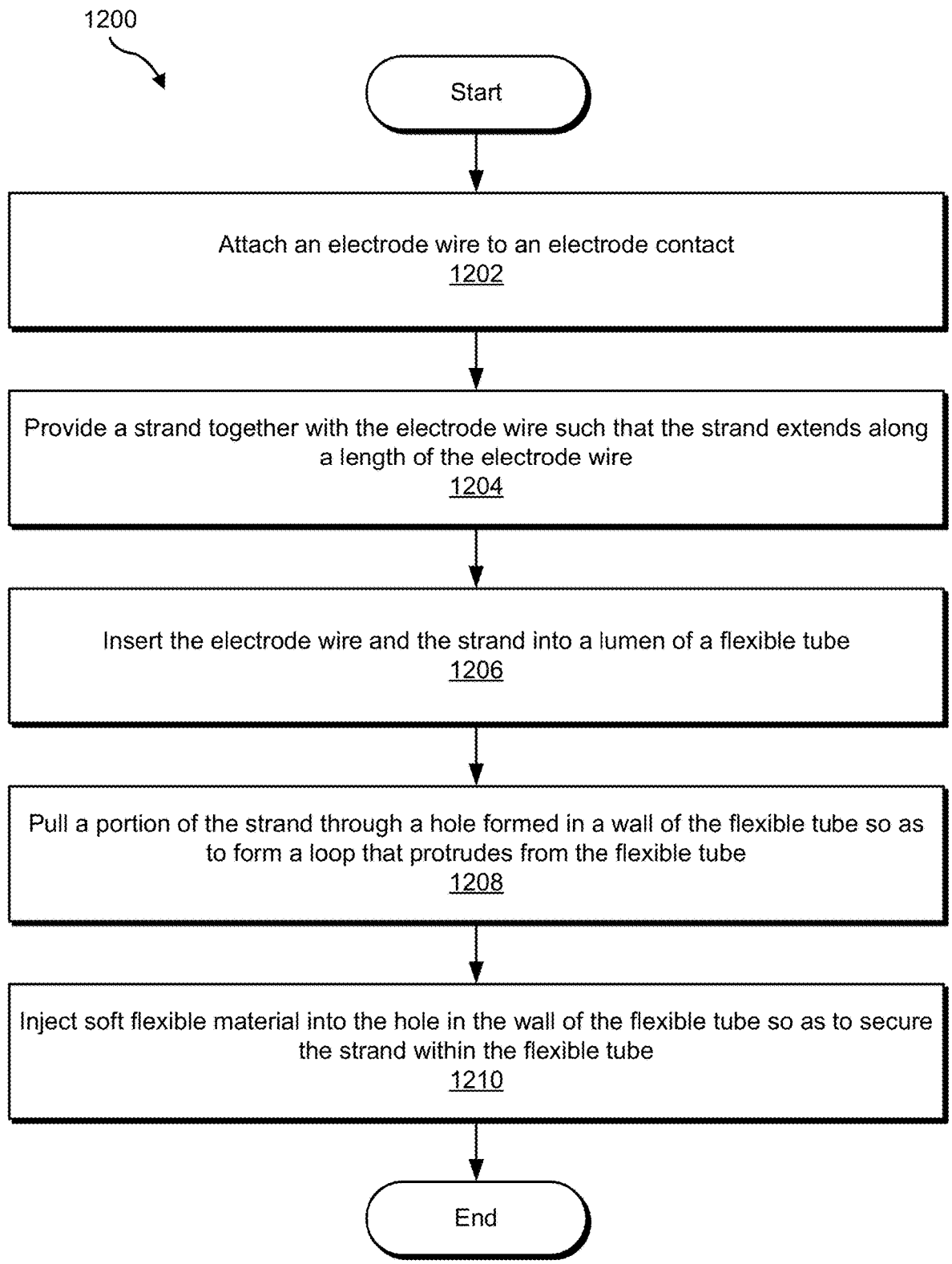
FIG. 12 shows an exemplary method for manufacturing an electrode lead configured to engage with a fixing element according to principles described herein.

FIG. 12 illustrates a method 1200 for manufacturing an electrode lead (e.g., electrode lead 110) configured to engage with a fixing element. While FIG. 12 illustrates exemplary operations according to one embodiment, other embodiments may omit, add to, reorder, and/or modify any of the operations shown in FIG. 12.

In operation 1202, an electrode wire is attached to an electrode contact (e.g., one of electrodes 112). The electrode wire may be attached in any suitable manner. For example, an electrode wire may be welded to each electrode contact included in a plurality of electrode contacts. Operation 1202 may be performed in any of the ways described herein.

In operation 1204, a strand is provided together with the electrode wire such that the strand extends along a length of the electrode wire. In certain examples, one or more additional strands may also be provided together with electrode wire. Operation 1204 may be performed in any of the ways described herein.

In operation 1206, the electrode wire and the strand are inserted into a lumen of a flexible tube. Operation 1206 may be performed in any of the ways described herein.

In operation 1208, a portion of the strand is pulled through a hole formed in a wall of the flexible tube so as to form a loop that is between the first end portion and the second end portion and that protrudes from the flexible tube. The loop is configured to engage with a fixing element that is configured to attach the loop to tissue within the recipient to secure the electrode lead within the recipient. In examples where an additional strand is provided, the additional strand may be pulled through a second hole in the wall of the flexible tube to form a second loop. The second hole may be spaced apart from the hole along the length of the flexible tube and/or about a circumference of the flexible tube. Operation 1208 may be performed in any of the ways described herein.

In operation 1210, a flexible insulating material (e.g., silicone) is injected into the hole formed in the wall of the flexible tube so as to secure the first end portion of the strand and the second end portion of the strand within the flexible tube. In certain examples, operation 1210 may also include filling the lumen of the flexible tube with the flexible insulating material. Operation 1210 may be performed in any of the ways described herein.

In certain alternative examples, a method for manufacturing an electrode lead (e.g., electrode lead 110) configured to engage with a fixing element may include using a mold to form a molded flexible body of the electrode lead. In such examples, the strand and electrode wire may be provided within an electrode lead mold. A portion of the strand may be provided through a hole in the electrode lead mold so as to form a loop outside of the electrode lead mold. The electrode lead mold may then be provided with a flexible insulating material (e.g., silicone) such that the electrode wire and certain portions of the strand are embedded within the flexible insulating material. The electrode lead mold may be provided with the flexible insulating material in any suitable manner. In certain examples, the flexible insulating material may be injected into the electrode lead mold such that the molded flexible body is formed when the flexible insulating material solidifies. In such examples, the flexible insulating material embeds the electrode wire and the portions of the strand other than the loop. Alternatively, the flexible insulating material may be compression molded in the electrode lead mold (e.g., by providing the flexible insulating material in a first half of the electrode lead mold and then pressing a second half of the electrode lead mold onto the flexible insulating material provided in the first half of the electrode lead mold).

In certain alternative examples, rather than (or in addition to) including one or more loops such as those described herein, an electrode lead (e.g., electrode lead 110) may be provided with one or more eyelets that are configured to engage with a fixing element to secure the electrode lead within the recipient. Such eyelets may correspond to tabs (e.g., triangular-shaped tabs, rectangular-shaped tabs, etc.) that may be integrally formed with and protrude from a flexible body of the electrode lead. Each eyelet includes a hole through which the fixing element such as a suture may be provided to secure the electrode lead within the recipient. Similar to the exemplary loops described herein, such eyelets may include a first eyelet, a second eyelet, and a third eyelet that are spaced apart from each other along a length of the flexible body and/or are radially separated from each other about a circumference of the flexible tube. With such a configuration, a surgeon may select the most convenient eyelet to engage with the fixing element without having to readjust (e.g., twist) the electrode lead to position the eyelet.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An electrode lead adapted for insertion into a recipient, comprising:
   a flexible body formed of a flexible insulating material;
   an electrode contact disposed on an outer surface of the flexible body; and
   a strand that includes
   a first end portion,
   a second end portion, and
   a loop that is provided between the first end portion and the second end portion and that protrudes from the flexible body,
   wherein
   the first end portion and the second end portion of the strand are embedded within the flexible body such that the first end portion is permanently fixed at a first position with respect to the flexible body prior to and after insertion of the electrode lead into the recipient and the second end portion is permanently fixed at a second position with respect to the flexible body prior to and after insertion of the electrode lead into the recipient,
   the loop is configured to engage with a fixing element that is configured to attach the loop to tissue within the recipient to secure the electrode lead within the recipient, and
   the loop protrudes from the flexible body at a position that has a predefined angular relationship with respect to a curved portion of the flexible body that includes the electrode contact.

2. The electrode lead of claim 1, wherein:
   the first end portion of the strand extends along a length of the flexible body in a first direction;
   the second end portion of the strand extends along the length of the flexible body in a second direction; and
   the first direction is opposite the second direction.

3. The electrode lead of claim 1, wherein:
   the first end portion and the second end portion are embedded within the flexible body; and
   the loop of the strand protrudes from the flexible body through a hole formed in the flexible body.

4. The electrode lead of claim 1, wherein the flexible body includes a plurality of reinforcing elements provided along a length of the flexible body in a region of the flexible body that includes the strand.

5. The electrode lead of claim 1, wherein:
   the strand further comprises a second loop that is provided between the loop and the second end portion and that protrudes from the flexible body; and
   the second loop is configured to engage with a second fixing element that is configured to attach the second loop to the tissue within the recipient to secure the electrode lead within the recipient.

6. The electrode lead of claim 5, wherein:
   the loop protrudes from the flexible body at a first location along a length of the flexible body; and
   the second loop protrudes from the flexible body at a second location along the length of the flexible body, the second location different than the first location.

7. The electrode lead of claim 6, wherein the first location is radially separated from the second location about a circumference of the flexible body.

8. The electrode lead of claim 7, wherein:
   the strand further comprises a third loop that is provided between the second loop and the second end portion and that protrudes from the flexible body; and the third loop is configured to engage with a third fixing element that is configured to attach the third loop to the tissue within the recipient to secure the electrode lead within the recipient.

9. The electrode lead of claim 8, wherein the third loop protrudes from the flexible body at a third location along the length of the flexible body, the third location different than the first location and the second location.

10. The electrode lead of claim 9, wherein the first location, the second location, and the third location are radially separated from each other about the circumference of the flexible body.

11. The electrode lead of claim 10, wherein:
the first location is radially separated from the second location by 120 degrees about the circumference of the flexible body;
the second location is radially separated from the third location by 120 degrees about the circumference of the flexible body; and
the third location is radially separated from the first location by 120 degrees about the circumference of the flexible body.

12. The electrode lead of claim 1, further comprising a second strand that includes
a third end portion,
a fourth end portion, and
a second loop that is provided between the third end portion and the fourth end portion and that protrudes from the flexible body,
wherein the second loop is configured to engage with a second fixing element that is configured to attach the second loop to tissue within the recipient to secure the electrode lead within the recipient.

13. The electrode lead of claim 12, further comprising a third strand that includes
a fifth end portion,
a sixth end portion, and
a third loop that is provided between the fifth end portion and the sixth end portion and that protrudes from the flexible body,
wherein the third loop is configured to engage with a third fixing element that is configured to attach the third loop to tissue within the recipient to secure the electrode lead within the recipient.

14. An electrode lead adapted for insertion into a recipient, comprising:
a flexible body formed of a flexible insulating material;
an electrode contact disposed on an outer surface of the flexible body; and
a plurality of separate strands, each strand included in the plurality of separate strands having
a first end portion,
a second end portion, and
a loop that is provided between the first end portion and the second end portion and that protrudes from the flexible body;
wherein
each first end portion and each second end portion of the plurality of strands are embedded within the flexible body such that each first end portion is permanently fixed at a position with respect to the flexible body prior to and after insertion of the electrode lead into the recipient and each second end portion is permanently fixed at another position with respect to the flexible body prior to and after insertion of the electrode lead into the recipient, each strand included in the plurality of separate strands is spaced apart in a longitudinal direction of the flexible body from an adjacent strand included in the plurality of separate strands,
each respective loop included in the plurality of separate strands is configured to engage with a fixing element that is configured to attach the respective loop to tissue within the recipient to secure the electrode lead within the recipient, and
the loop of a strand included in the plurality of separate strands protrudes from the flexible body at a position that has a predefined angular relationship with respect to a curved portion of the flexible body that includes the electrode contact.

15. The electrode lead of claim 14, wherein:
the plurality of separate strands includes a first strand, a second strand, and a third strand;
the loop of the first strand protrudes from the flexible body at a first location about a circumference of the flexible body;
the loop of the second strand protrudes from the flexible body at a second location about the circumference of the flexible body, the second location different than the first location; and
the loop of the third strand protrudes from the flexible body at a third location about the circumference of the flexible body, the third location different than the first location and the second location.

16. The electrode lead of claim 15, wherein:
the first location is radially separated from the second location by 120 degrees about the circumference of the flexible body;
the second location is radially separated from the third location by 120 degrees about the circumference of the flexible body; and
the third location is radially separated from the first location by 120 degrees about the circumference of the flexible body.

17. The electrode lead of claim 14, wherein the flexible body includes a plurality of reinforcing elements provided along a length of the flexible body in a region of the flexible body that includes the plurality of separate strands.

18. A method of manufacturing an electrode lead adapted for insertion in a recipient, the method comprising:
attaching an electrode wire to an electrode contact;
providing a strand together with the electrode wire such that the strand extends along a length of the electrode wire, the strand having a first end portion and a second end portion;
inserting the electrode wire and the strand into a lumen of a flexible tube;
pulling a portion of the strand through a hole formed in a wall of the flexible tube so as to form a loop that is between the first end portion and the second end portion and that protrudes from the flexible tube; and
injecting soft flexible material into the hole formed in the wall of the flexible tube so as to secure the first end portion of the strand and the second end portion of the strand within the flexible tube,
wherein
the first end portion and the second end portion of the strand are embedded within the flexible tube by the soft flexible material such that the first end portion is permanently fixed at a first position within the flexible tube prior to and after insertion of the electrode lead into the recipient and the second end portion is permanently fixed at a second position within the flexible tube prior to and after insertion of the electrode lead into the recipient, the loop is configured to engage with a fixing element that is configured to attach the loop to tissue within the recipient to secure the electrode lead within the recipient, and the loop protrudes from the flexible tube at a position that has a predefined angular relationship with respect to a curved portion of the flexible tube that includes the electrode contact.

19. The method of claim 18, wherein:

the providing of the strand together with the electrode wire includes providing a second strand together with the electrode wire such that the second strand extends along the length of the electrode wire, the second strand having a third end portion and a fourth end portion;

the inserting the electrode wire and the strand into the lumen of the flexible tube includes inserting the second strand into the lumen; and the method further comprises pulling a portion of the second strand through a second hole formed in the wall of the flexible tube so as to form a second loop that is between the third end portion and the fourth end portion and that protrudes from the flexible tube.

20. The method of claim 19, wherein the hole formed in the wall of the flexible tube is radially separated from the second hole formed in the wall of the flexible tube about a circumference of the flexible tube.

\* \* \* \* \*